United States Patent [19]

Murakami et al.

[11] 3,951,954
[45] Apr. 20, 1976

[54] NOVEL OXOFURYL ESTER DERIVATIVES OF PENICILLIN AND CEPHALOSPORIN

[75] Inventors: Masuo Murakami, Tokyo; Ichiro Isaka, Hoya; Teruya Kashiwagi, Ageo; Hidefumi Matsui, Ageo; Kohzi Nakano, Ageo; Kozo Takahashi; Hiroshi Horiguchi, both of Tokyo; Akio Koda, Hoya, all of Japan

[73] Assignee: Yamanouchi Pharmaceutical Co., Ltd., Tokyo, Japan

[22] Filed: Feb. 18, 1975

[21] Appl. No.: 550,457

Related U.S. Application Data

[63] Continuation of Ser. No. 256,343, May 24, 1972, abandoned.

[30] Foreign Application Priority Data

| June 5, 1971 | Japan | 46-39483 |
| June 15, 1971 | Japan | 46-42197 |
| June 25, 1971 | Japan | 46-46510 |
| Aug. 10, 1971 | Japan | 46-59969 |
| Mar. 11, 1972 | Japan | 47-25121 |

[52] U.S. Cl. .................. 260/239.1; 260/243 C; 424/246; 424/271
[51] Int. Cl.² .................................. C07D 499/68
[58] Field of Search .................................. 260/239.1

[56] References Cited
UNITED STATES PATENTS

| 2,985,648 | 5/1961 | Doyle et al. | 260/239.1 |
| 3,641,001 | 2/1972 | Love et al. | 260/239.1 |
| 3,647,783 | 3/1972 | Pirie | 260/239.1 |
| 3,697,507 | 10/1972 | Frederiksen et al. | 260/239.1 |
| 3,860,579 | 1/1975 | Ferres et al. | 260/239.1 X |

Primary Examiner—Gerald A. Schwartz
Attorney, Agent, or Firm—Burgess Ryan and Wayne

[57] ABSTRACT

The oxofuryl ester derivatives of 6-($\alpha$-aminophenylacetamido)penicillanic acid, 7-($\alpha$-aminophenylacetamido)-cephalosporanic acid, or 7-($\alpha$-aminophenylacetamide)desacetoxycephalosporanic acid represented by the general formula

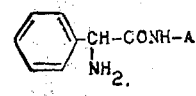

wherein A represents

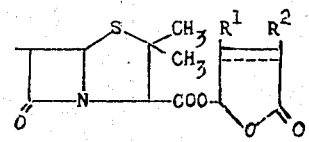

or

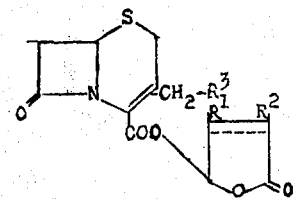

wherein $R^1$ and $R^2$, which may be the same or different, each represents a hydrogen atom or a lower alkyl group, said $R^1$ and $R^2$ may form together a 1,3-butadienylene group, $R^3$ represents a hydrogen atom or an acetoxy group, and ‾‾‾‾‾‾‾ means a single bond or a double bond, and acid addition salts of them. When those compounds are orally administered, they are readily absorbed by the intestines and show antibacterial activity by splitting their ester bonds. The rate of absorption of the compounds by the intestines are higher and the toxic property of them is less than those of known compounds similar to the above compounds.

5 Claims, No Drawings

NOVEL OXOFURYL ESTER DERIVATIVES OF PENICILLIN AND CEPHALOSPORIN

This is a continuation of application Ser. No. 256,343, filed May 24, 1972, now abandoned.

BACKGROUND OF THE INVENTION

The present invention relates to the oxofuryl ester derivatives of 6-(α-aminophenylacetamido)penicillanic acid, 7-(α-aminophenylacetamido)cephalosporanic acid, or 7-(α-aminophenylacetamido)desacetoxycephalosporanic acid represented by the general formula

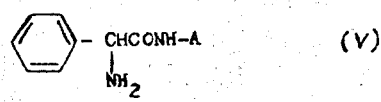

wherein A represents

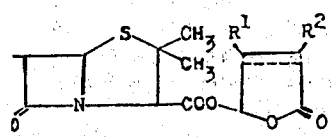

or

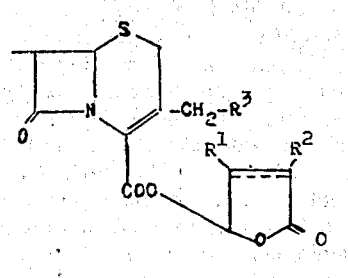

wherein $R^1$ and $R^2$, which may be the same or different, each represents a hydrogen atom or a lower alkyl group, said $R^1$ and $R^2$ may form together a 1,3-butadienylene group, $R^3$ represents a hydrogen atom or an acetoxy group, and ═══ means a single bond or a double bond, and the acid addition salts thereof.

When the compounds of this invention are orally administered, they are readily absorbed by intestines and show antibacterial activity by splitting the ester bonds in the body.

Although 6-(α-aminophenylacetamido)penicillanic acid (hereinafter, the acid is called "ampicillin") is well known as a semi-synthetic penicillin that can be orally administered, the extent of the absorption by oral administration is not necessarily sufficient and thus it has been desired to increase the amount of ampicillin to be absorbed by oral administration. As ampicillin derivatives fulfil the above desire, the acyloxymethyl ester of ampicillin, in particular, the pivaloyloxymethyl ester of ampicillin (hereinafter, the ester is called "pivampicillin") has been developed (Belgian Pat. No. 721,525 and Jour. Med. Chem., 13, 607-612(1970)).

Also, the acyloxymethyl esters of 7-(α-aminophenylacetamido)cephalosporanic acid (hereinafter, the acid is called "cephaloglycin") and 7-(α-aminophenylacetamido)desacetoxycephalosporanic acid (hereinafter, the acid is called "cephalexin") have been developed as the readily absorbable derivatives of the acids (German Offenlegungsschriften Nos. 1,904,585 and 1,951,012).

It has been said that each of the acyloxymethyl esters as mentioned above be absorbed in the intestines and hydrolyzed enzymatically to isolate formaldehyde and the acid and to show antibacterial acitivity as ampicillin, cephaloglycin or cephalexin. Thus, the problem of increasing the absorption of ampicillin, cephaloglycin, or cephalexin by oral administration may be once at least solved by the discovery of the acyloxymethyl esters of them but those acyloxymethyl esters have not yet been practically used as medicaments since the presence of hepatotoxicity has unfortunately been found in the step of the toxicological evaluation (Antimicrobial Agents and Chemotherapy — 1970, pages 442–454, in particular, page 453). There are no descriptions about the cause of the hepatotoxicity in the above literature but it has hitherto been known that formaldehyde shows high toxic property (about 50 times) as compared with those of other aldehydes having molecular weights larger than that of formaldehyde (Chemical Abstracts, 45, 4824h (1951) and ibid., 55, 8653d (1961) ) and also it gives bad influences on a liver (Biochem. Pharmacol., 16, 1533–1537 (1967); Chemical Abstracts, 69, 58092x (1968); and Biochem. Jour., 111, 665–678 (1969) ). Upon considering those facts, the inventors have noticed that the cause of the hepatotoxicity is based on the formaldehyde liberated from the acyloxymethyl ester in the body and have discovered as the results of the investigations of the readily absorbable derivatives of cephaloglycin or cephalexin which will not liberate formaldehyde in the body that the novel oxofuryl ester compounds represented by the aforesaid general formula V are readily absorbed in the intestines when they are orally administered and converted into ampicillin, cephaloglycin or cephalexin by splitting enzymatically their ester bonds in blood to show antibacterial activity.

It has never been anticipated from the prior arts that the oxofuryl esters show good absorbable property in intestines by oral administration and give a high concentration thereof in blood in spite of the great different structures thereof from those of the known acyloxymethyl esters.

It will be clear from the chemical structure of the compound that the oxofuryl ester of this invention does not release formaldehyde or similar aldehydes in the body, which is one of the features of this invention. Moreover, the compounds of this invention are stable to β-lactamase, which is other feature of this invention.

Thus, the problem of obtaining the derivatives of penicillin and cephalosporin having no toxicity and showing good absorbable property in intestines by oral administration has been solved by the present invention.

SUMMARY OF THE INVENTION

The compounds of this invention may be prepared by various manners but it is preferable to use, as the starting material, the novel oxofuryl ester compound prepared by reacting an alkali metal salt of a natural penicillin such as benzylpenicillin, phenoxypenicillin, 7-phenylacetamidodesacetoxycephalosporanic acid, or cephalosporin C with the oxofuryl halide represented by the formula

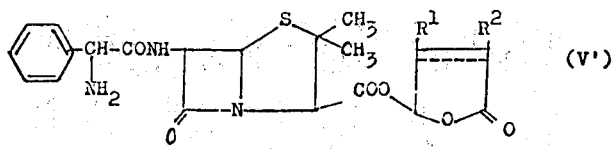

or

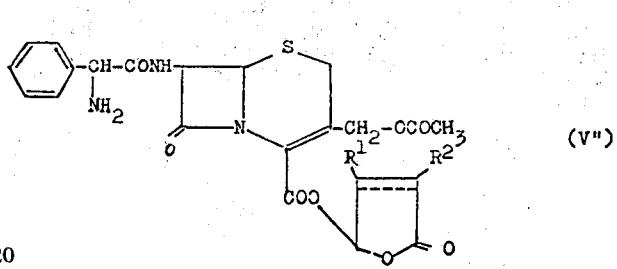

respectively
wherein R¹ and R² are as above defined, may be prepared by the manner disclosed in the specification of German Offenlegungsschrift No. 2,029,195 using, as the starting material, the oxofuryl ester compound of the formula II shown below of penicillin or cephalosporin respectively.

That is, the ester compound of penicillin or cephalosporin is caused to react with a phosphorous halide in an inert solvent in the presence of a tertiary amine. Examples of the inert solvent used in the above reaction are toluene, chloroform, dichloromethane, dichloroethane, trichloroethylene, etc. As the tertiary amines, there are illustrated pyridine, N,N-dimethylaniline, triethylamine, etc., but the use of aromatic amines such as N,N-dimethylaniline is particularly preferable. Also, as the phosphorous halide, there are illustrated phosphorus pentachloride, phosphorus pentabromide, etc., but the use of phosphorus pentachloride is particularly preferable.

For example, the reaction is conducted under cooling, preferably at temperatures from 0°C to −30°C when phosphorus pentachloride is employed. The amount of the tertiary amine is preferably 3–5 mols per mol of phosphorus pentachloride. It is also preferable to use the phosphorus halide in an amount of slightly excessive to the starting material.

Then, the iminohalide compound obtained in the above reaction is, without being isolated from the reaction product, caused to react with a lower alcohol to form an iminoether compound. As the lower alcohol, a lower aliphatic alcohol such as methanol, ethanol, propanol, etc., may be used. It is preferable to use a slightly excessive amount of the lower alcohol to the starting material and also to conduct the reaction at almost same temperature as in the case of forming the iminohalide compound.

Thereafter, the product prepared above is caused to react with phenylglycine or a reactive derivative thereof. A preferable reactive derivative of phenylglycine is phenylglycylchloride hydrochloride but other acid halides, acid anhydrides, mixed acid anhydrides, etc., may also be used in this invention.

In the case of using phenylglycylchloride hydrochloride, it is preferable to add to a solution containing the iminoether the hydrochloride in an equimolar or slightly excessive amount to the iminoether compound and to conduct the reaction at a temperature almost same as that in the previous reaction step. Also, it is preferable for conducting smoothly the reaction to add

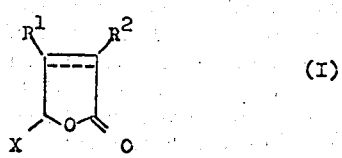

wherein X represents a halogen atom; R¹ and R² are as above defined in a conventional manner.

In addition, the compounds of the formula I may be prepared by the following manners. For example, γ-chloro-γ-butyrolactone

is prepared by the reaction of succinyl dichloride and tri-n-butyltin hydride ($Bu_3SnH$) followed by distillation (Jour. Org. Chem., 25, 284–285 (1960) ), 2-bromo-5-oxo-2,5-dihydrofuran

is prepared by reacting 2-acetoxyfuran and bromine (Chemical Abstracts, 47, 7481h (1953) and Acta Chem. Scand., 6, 565–568 (1952), and 1-bromo-3-oxoisobenzofuran

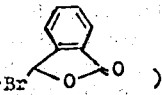

is prepared by reacting phthalide and bromine (Org. Syn., Coll., Vol. III, 737–738 (1955) ). Furthermore, 2-bromo-3-ethyl-4-methyl-5-oxo-2,5-dihydrofuran

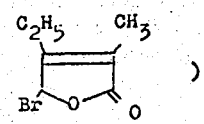

is prepared by reacting 3-ethyl-2-hydroxy-4-methyl-5-oxo-2,5-dihydrofuran (Chemical Abstracts, 63, 11352h (1965) and Bull. soc. chim. France, 1965(8), 2242–2249) and phosphorus tribromide. The above compound having, as substituents, the alkyl groups at the 3- and 4-positions thereof is a novel compound and thus the production thereof is illustrated practically in the example of this invention.

Now, the general processes of producing the novel compounds of this invention will be described below.

a. The oxofuryl ester of ampicillin or cephaloglycin represented by the formula a tertiary amine such as pyridine, N,N-dimethylaniline, etc., to the reaction system.

Finally, the addition compound obtained by the above reaction is treated with water or alcohol. The water treatment may be conducted together with the isolation of the aimed material. That is, water or a saturated aqueous solution of sodium chloride is added to the reaction product obtained in the previous step and then the aqueous layer formed is separated from the organic solvent layer. The organic solvent layer thus separated is dehydrated and concentrated under reduced pressure and the oily residue thus formed is dissolved in water. The solution is, then, washed with a lower alkyl ester of acetic acid, methylisobutyl ketone, etc., and after subjecting the solution to salting out process, the oily or crystalline precipitate thus formed is extracted with a suitable organic solvent such as ethyl acetate, dichloroethane, etc. Then, by subjecting the extract to a treatment such as concentration and re-crystallization by a conventional manner, the hydrochloride of the aimed material of the formula V' or V'' is obtained as the crystal thereof. Also, by treating the extract obtained above with an aqueous solution of a weak basic material such as sodium bicarbonate and then subjecting the extract to concentration or recrystallization by a conventional manner, the aimed material of the formula V' or V'' may be isolated.

The aimed material thus isolated may be converted into a salt of other acid if necessary.

b. The oxofuryl ester compound of the formula II of natural penicillin is caused to react with perbenzoic acid or performic acid according to the method disclosed in the specification of U.S. Pat. No. 3,275,626, etc., to form an S-oxide compound of the formula II' shown below. Then, by heating the S-oxide compound in the presences of an inorganic or organic acid such as phosphoric acid, sulfuric acid, phenyl dihydrogenphosphoric acid, p-toluene sulfonic acid, etc., and a weak base such as pyridine, quinoline, benzimidazole, the ring of the compound is enlarged and thus 7-acylaminodesactoxycephalosporanic acid ester of the formula II'' shown below is obtained.

By following the same procedure as in the method (a) mentioned above using the ester II'' as the starting material, oxofuryl ester of cephalexin shown by the formula

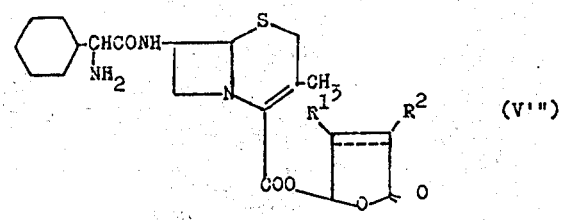

wherein $R^1$ and $R^2$ are as above defined, is obtained.

c. The compound V of the present invention may further be obtained by reacting 6-aminopenicillanic acid, 7-aminocephalosporanic acid, or 7-aminodesacetoxycephalosporanic acid and the oxofuryl halide of the formula I as described above to form the ester thereof and acylating the ester with a reactive derivative of phenylglycine such as phenylglycylchloride hydrochloride by a conventional manner.

An example of the production step of the compounds of this invention can be illustrated by the following reaction formula.

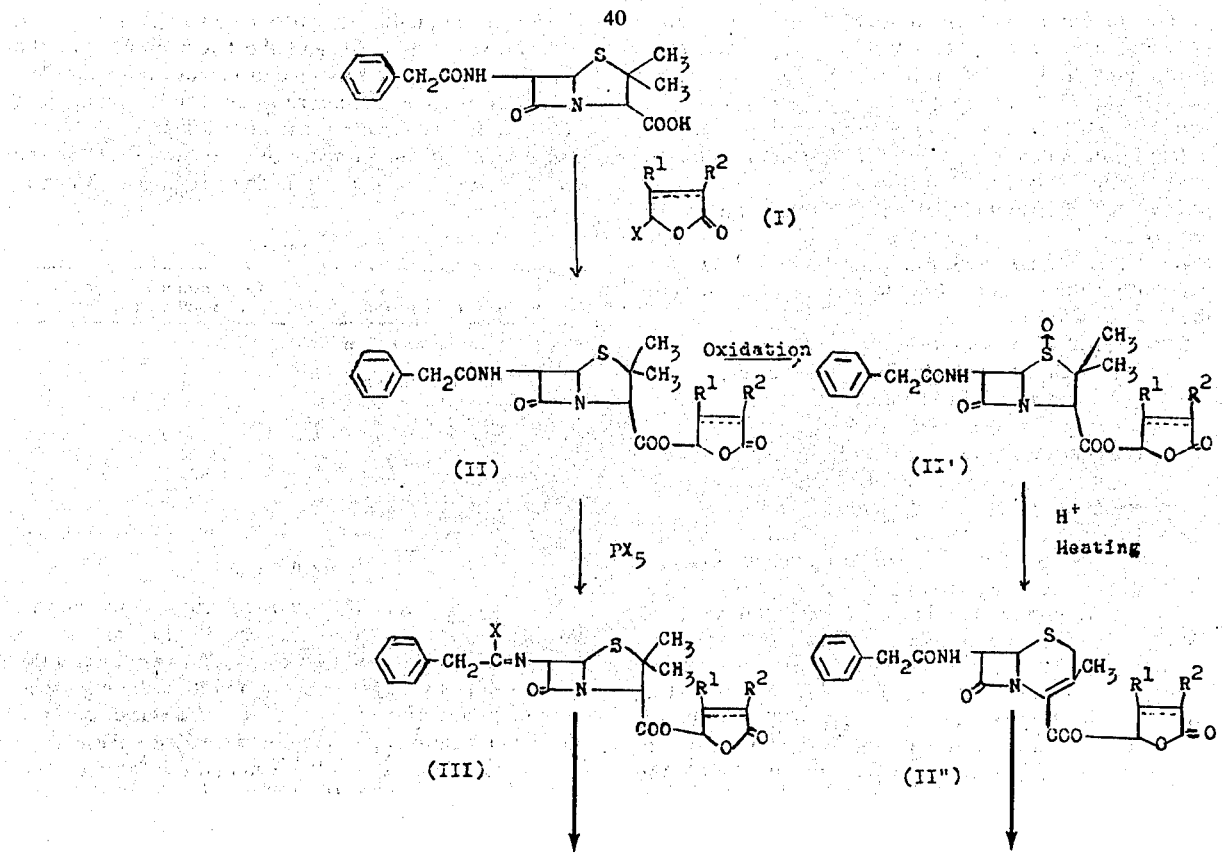

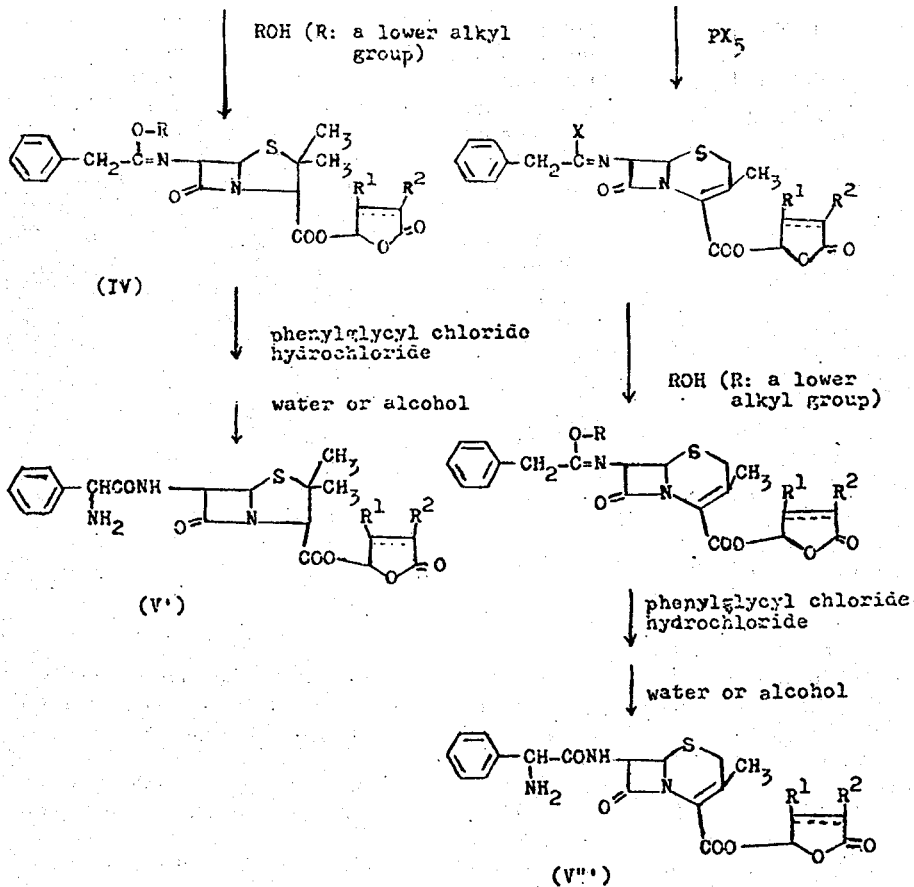

In the above formulae, R¹ and R² are as above defined and X represents a halogen atom.

Now, the examples of the lower alkyl group represented by the substituents R¹ and R² of the compound of this invention include a methyl group, an ethyl group, an isopropyl group, a n-butyl group, a tert-butyl group, and the like. When R¹ and R² form together a 1,3-butadienylene group, the ester portion forms, as a whole, 1-oxo-1,3-dihydro-isobenzofuran-3-yl ester.

The compounds V of this invention include practically the oxofuryl esters of 6-(α-aminophenylacetamido)penicillanic acid (ampicillin), 7-(α-aminophenylacetamido)cephalosporanic acid (cephaloglycin) and 7-(α-aminophenylacetamido)desacetoxycephalosporanic acid (cephalexin). For example, there are illustrated 5-oxo-tetrahydro-2-furyl ester,
1-oxo-1,3-dihydro-isobenzofuran -3-yl ester,
5-oxo-2,5-dihydro-2-furyl ester,
3,4-dimethyl-5-oxo-2,5-dihydro-2-furyl ester,
3-ethyl-4-methyl-5-oxo-2,5-dihydro-2-furyl ester,
3-methyl-4-propyl-5-oxo-tetrahydro-2-furyl ester,
3-n-butyl-4-ethyl-5-oxo-tetrahydro-2-furyl ester,
3,4-diethyl-5-oxo-tetrahydro-2-furyl ester,
3-ethyl-4-propyl-5-oxo-2,5-dihydro-2-furyl ester,
3-methyl-4-tert-butyl-5oxo-2,5-dihydro-2-furyl ester.

The above compounds may also be obtained as the salts of mineral acids such as hydrochloric acid.

Now, for showing the excellent properties of the compounds of this invention, the experiments of testing the concentration of the compound in blood when it was orally administered and the results thereof are shown in the following examples together with the results of the tests made about ampicillin and pivampicillin.

Experiment a.

Each of ampicillin tri-hydrate, pivampicillin hydrochloride-mono-hydrate, and the hydrochloride of the aimed compound of this invention was orally administered to rats (male, each group five rats) in an amount of 20 mg/kg as ampicillin and after 0.5 hour, the blood was drawn and the concentration of ampicillin in the blood plasma was measured. The results are shown in the following table.

Table I

| Administered material | Concentration of ampicillin in blood plasma (γ/ml) |
|---|---|
| Ampicillin tri-hydrate(known product) | 1.00 |
| Pivampicillin hydrochloride mono-hydrate (known product) | 3.80 |
| Ampicillin 5-oxo-tetrahydro-2-furyl ester hydrochloride (product of Example 1) | 4.60 |
| Ampicillin 1-oxo-1,3-isobenzofuran-3-yl ester hydrochloride (product of Example 2) | 5.58 |

Experiment b.

Each of pivampicillin hydrochloride mono-hydrate and the hydrochloride of the aimed compound of this invention was orally administered to beagle dogs (male, each group six dogs) in an amount of 20 mg/kg as ampicillin and after 0.5 hour, the blood was drawn and the concentration of ampicillin in the blood plasma was measured. The results are shown in the following table.

Table II

| Administered material | Concentration of ampicillin in blood plasma (γ/ml) |
| --- | --- |
| Pivampicillin hydrochloride mono-hydrate (known product) | 2.29 (1.00)* |
| Ampicillin 3,4-dimethyl-5-oxo-2,5-dihydro-2-furyl ester hydrochloride (product of Example 6) | 4.08 (1.78) |
| Ampicillin 3-ethyl-4-methyl-5-oxo-2,5-dihydro-2-furyl ester hydrochloride (product of Example 7) | 4.44 (1.94) |

*The values in the parentheses are ratios.

EXAMPLE 1 a. After suspending 6.17g of benzylpenicillin potassium and 0.4g of anhydrous potassium bicarbonate in 30 ml of dimethylformamide, 2.0g of 5-chloro-γ-butyrolactone was added to the suspension with stirring at room temperature over a period of 30 minutes and the mixture was further stirred for 5 hours at room temperature. After the reaction was over, the reaction mixture was dispersed in ice water on which ethyl acetate had been added in layer. The ethyl acetate layer was recovered, washed with 5% aqueous solution of sodium bicarbonate and then water, and dried over anhydrous sodium sulfate. By distilling off the solvent from the ethyl acetate solution, 5g of yellowish oily benzylpenicillin-5-oxo-tetrahydro-2-furyl ester was obtained.

Infrared absorption spectra: $\nu$NH: 3550 cm$^{-1}$ (—HN—), $\nu$CO: 1800–1770 cm$^{-1}$ broad (lactone, β-lactam, ester), $\nu$C = 0 : 1665 cm$^{-1}$ (amide).

b. After dissolving 4.9g of benzylpenicillin 5-oxo-tetrahydro-2-furyl ester in 49 ml of dichloroethane, 4.81 ml of N,N-dimethylaniline was added to the solution and the mixture was cooled to −25°C. Then, 2.69g of phosphorus pentachloride was added to the solution and the mixture was stirred for one hour and 40 minutes at −25°C ± 5°C. Thereafter, by adding dropwise 47 ml of methanol to the mixture at the same temperature as above and stirring the mixture for further 3 hours, a solution containing the iminoether compound thus formed was obtained. After adding to the solution 8.02 ml of N,N-dimethylaniline, 2.82g of D(−)-α-phenylglycylchloride hydrochloride was added little by little to the mixture with stirring over one hour period at −25°C ± 5°C. Thereafter, the mixture was stirred for 2 hours at the same temperature as above. The reaction mixture was allowed to stand overnight at −25°C.

To the reaction mixture was added 23 ml of water and after stirring the mixture for 30 minutes at 0°C, perlite (made by Toko Perlite K.K.) was added to the mixture and the mixture was filtered. The filtrate was allowed to stand to form an aqueous layer and an organic layer. The product in the organic layer was extracted twice each 10 ml of water and the extracts were combined with the aqueous layer.

The aqueous solution thus obtained was washed with dichloroethane, the pH of the solution was adjusted to 7 with the addition of sodium bicarbonate, and then the product in the solution was extracted with dichloroethane. The dichloroethane extract was washed with water, dried over anhydrous sodium sulfate, and then concentrated under reduced pressure at a low temperature. When 5 ml of ethyl acetate was added to the oily residue thus obtained, it was crystallized. After adding further to the mixture 20 ml of ether and cooling the mixture, the crystals were recovered by filtration to provide 2.7g of the white acicular crystals of ampicillin 5-oxo-tetrahydro-2-furyl ester having a melting point of 181°–182°C (decomposed).

After dissolving 2.1g of ampicillin 5-oxo-tetrahydro-2-furyl ester prepared above in methylene chloride, the solution was cooled to 0°C and about 1.5 ml of isopropyl alcohol saturated with hydrogen chloride was added dropwise to the solution with stirring to adjust the pH of the solution to 3.

Then, by further stirring the mixture for 10 minutes and then adding 30 ml of ether to the mixture, crystals were precipitated. The crystals were recovered by filtration to provide 2.2g of the white crystals of ampicillin 5-oxo-tetrahydro-2-furyl ester hydrochloride having a melting point of 144°–146°C (decomposed).

Infrared absorption spectra: $\nu$NH$_3^+$ : 3200 cm$^{-1}$, $\nu$NH$_2^+$ : 2700–2600 cm$^{-1}$, $\nu$C = 0 : 1800 − 1760 cm$^{-1}$ broad (β-lactam, lactone, ester), $\nu$C = 0 : 1685 cm$^{-1}$ (amide).

| Elemental analysis as C$_{20}$H$_{23}$O$_6$N$_3$S.HCl: | | | |
| --- | --- | --- | --- |
| | C(%) | H(%) | N(%) | Cl(%) |
| Calculated: | 51.12 | 5.15 | 8.94 | 7.54 |
| Found: | 50.87 | 5.62 | 8.40 | 7.29 |

EXAMPLE 2 a. After suspending 11.2g of benzylpenicillin potassium in 50 ml of dimethylformamide, 1.5g of sodium bicarbonate and 6.4g of 1-bromo-3-oxo-1,3-dihydro-isobenzofuran were added to the suspension and the mixture was stirred for 16 hours at room temperature. The reaction mixture was dispersed in 100 ml of ice water and the product was extracted thrice each with 50 ml of ethyl acetate. The ethyl acetate extracts were combined each other and the mixture was washed with 5% aqueous solution of sodium bicarbonate and then water, dried over anhydrous magnesium sulfate, and then concentrated under reduced pressure at a low temperature. By recrystallizing, the residue thus obtained from a mixture of ethyl acetate and ether, 13.3g of the white crystals of benzylpenicillin 1-oxo-1,3-dihydro-isobenzofuran-3yl ester having a melting point of 178–180°C. The yield for the product was 95.1%.

| Elemental analysis as C$_{24}$H$_{22}$O$_6$N$_2$S: | | | |
| --- | --- | --- | --- |
| | C(%) | H(%) | N(%) | S(%) |
| Calculated: | 61.79 | 4.75 | 6.00 | 6.87 |
| Found: | 61.52 | 4.93 | 5.88 | 6.50 | b. After dissolving 4.7g of the benzylpenicillin 1-oxo-1,3-dihydro-isobenzofuran-3-yl ester prepared above in 50 ml of dichloromethane, 4.12 ml of N,N-dimethylaniline was added to the solution and the reaction mixture was cooled to −25°C.

Then, 2.3g of phosphorus pentachloride was added to the mixtures and the resultant mixture was stirred for 1.5 hours at −25°C ± 5°C. By adding dropwise 40 ml of methanol to the mixture at the same temperature as above and stirring the mixture for further 2.5 hours, a solution containing the iminoether thus formed was obtained. After adding 6.86 ml of N,N-dimethylaniline to the solution, 2.5g of D(−)-α-phenylglycylchloride hydrochloride was added in a few portions over one hour period. Thereafter, the mixture was stirred for 2 hours at the same temperature and then the reaction mixture was allowed to stand for 16 hours at a temperature of −20°C to −25°C. The reaction mixture was mixed with 50 ml of cold saturated aqueous solution of sodium chloride and after stirring the mixture sufficiently at temperatures lower than 0°C, the mixture was allowed to stand to form an aqueous layer and a dichloromethane layer, the former was separated from the latter. The dichloromethane layer was washed with cold saturated aqueous solution of sodium chloride, dried over anhydrous magnesium sulfate, and then concentrated under reduced pressure at a low temperature to provide an oily residue. The residue was washed with about 50 ml of ether and after recovering the insoluble solid matters by filtration, the solid matters were dissolved in 50 ml of water. The aqueous solution was washed with 30 ml of ethyl acetate and saturated with sodium chloride, and the oily material thus formed was extracted twice each with 30 ml of dichloromethane. The dichloromethane extracts were combined each other, washed twice with saturated aqueous solution of sodium chloride, dried over anhydrous sodium sulfate, and concentrated under reduced pressure at a low temperature. When ether was added to the residue thus formed and the mixture was stirred, crystals were precipitated. The crystals were recovered by filtration, washed with a small amount of ether, and dried to provide 3.7g of the white powder of ampicillin 1-oxo-1,3-dihydroisobenzofuran-3-yl ester hydrochloride having a melting point of 154°–157°C (decomposed). The yield for the product was 71%.

Elemental analysis as $C_{24}H_{24}O_6N_3SCl$:

| | C(%) | H(%) | N(%) | Cl(%) |
|---|---|---|---|---|
| Calculated: | 55.65 | 4.67 | 8.11 | 6.84 |
| Found: | 55.27 | 4.95 | 7.84 | 6.35 |

EXAMPLE 3 a. After suspending 8.63g of 6-aminopenicillanic acid in 50 ml of dimethylformamide, 8.3 ml of triethylamine was added to the suspension with stirring at temperatures lower than 10°C. To the solution thus formed was added dropwise 9.6g of 5-chloro-γ-butyrolactone at 10°C with stirring and thereafter the mixture was stirred for 2 hours at room temperature.

To the reaction mixture was added 100 ml of ethyl acetate and the triethylamine hydrochloride thus formed was filtered off. The filtrate was washed twice each with 30 ml of saturated aqueous solution of sodium chloride, washed with 50 ml of 5% aqueous solution of sodium bicarbonate and then 50 ml of saturated aqueous solution of sodium chloride successively, dried over anhydrous sodium sulfate, and then the solvent was distilled off under reduced pressure and a low temperature. The oily residue thus formed was washed with petroleum ether and dried under reduced pressure to provide 9.2% of viscous 6-aminopenicillanic acid 5-oxo-tetrahydro-2-furyl ester with a yield of 76.7%.

Infrared absorption spectra: $\nu NH_2$ : 3350 cm$^{-1}$ and $\nu C = O$ : 1800–1760 cm$^{-1}$ broad (β-lactam, lactone and ester).

b. After dissolving 3.0g of 6-aminopenicillanic acid 5-oxo-tetrahydro-2-furyl ester in 30 ml of dichloromethane, 2.5g of D(−)-α-phenylglycylchloride hydrochloride and 20 ml of dichloromethane containing 1.4 ml of triethylamine were added alternately to the solution to maintain the solution at a weak acid state (so that a pH test paper wetted with water to show about 3 in pH when the reaction mixture was brought into contact with the test paper).

Thereafter, the mixture was stirred for 2 hours at the same temperature as above, 30 ml of water was added to the reaction mixture with stirring, and perlite (made by Toko Perlite K.K.) was added. Then the perlite was filtered off and the aqueous layer thus formed was separated from the filtrate. The remaining organic layer was extracted twice each with 10 ml of water and then the aqueous extracts were combined with the separated aqueous layer above. After washing the aqueous solution thus obtained with dichloroethane, the pH of the solution was adjusted to 7 by adding sodium bicarbonate and then the product was extracted with dichloroethane. The dichloroethane extract was washed with water, dried over anhydrous sodium sulfate, and concentrated under reduced pressure at a low temperature. When 5 ml of ethyl acetate was added to the oily residue thus formed, crystals were formed. After adding 20 ml of ether to the mixture and cooling the reaction mixture, the crystals were recovered by filtration to provide 2.3g of the white acicular crystals of ampicillin 5-oxo-tetrahydro-2-furyl ester having a melting point of 181°–182°C (decomposed). The yield of the product was 53.1%.

c. After dissolving 2.2g of the ampicillin 5-oxo-tetrahydro-2-furyl ester prepared above in methylene chloride, the solution was cooled to 0°C and then isopropyl alcohol saturated with hydrogen chloride was added dropwise to the solution with stirring to adjust the pH thereof to 3. After stirring the mixture for 10 minutes at the same temperature as above, 30 ml of ether was added to the mixture, whereby crystals were precipitated. By recovering the crystals by filtration, 2.3g of the white powdery crystals of ampicillin 5-oxo-tetrahydro-2-furyl ester hydrochloride having a melting point of 144°–146°C (decomposed) was obtained, the yield thereof being 96.4%.

Infrared absorption spectra: $\nu NH_3^+$ : 3200 cm$^{-1}$, $\nu NH_2^+$ : 2700–2600 cm$^{-1}$ $\nu C = O$ : 1800–1760 cm$^{-1}$ broad (β-lactam, lactone and ester), $\nu C = O$ : 1685 cm$^{-1}$ (amide)

Elemental analysis as $C_{20}H_{23}N_3O_6S.HCl$:

| | C(%) | H(%) | N(%) | Cl(%) |
|---|---|---|---|---|
| Calculated: | 51.12 | 5.15 | 8.94 | 7.54 |
| Found: | 51.01 | 5.62 | 8.82 | 7.34 |

EXAMPLE 4 a. After suspending 8.63 g of 6-aminopenicillanic acid in 50 ml of dimethylformamide, 8.3 ml of triethylamine was added to the suspension and the mixture was stirred at temperatures lower than 10°C to form a solution. To the solution was added 12.8g of 1-bromo-3-oxo-1,3-dihydroisobenzofuran and the mixture was stirred for 16 hours at room temperature. To the reaction mixture was added 100 ml of ethyl acetate and then the triethylamine hydrobromide thus precipitated was filtered off. The filtrate was washed twice each with 30 ml of saturated aqueous solution of sodium chloride, washed with 50 ml of 5% aqueous solution of sodium bicarbonate and then 50 ml of saturated aqueous solution of sodium chloride, dried over anhydrous sodium sulfate, and then the solvent was distilled off under reduced pressure at a low temperature. The residue was washed with a small amount of ether to provide 11.5g of viscous 6-aminopenicillanic acid 1-oxo-1,3-dihydro-isobenzofuran-3-yl ester with a yield of 82.7%.

Infrared absorption spectra: $\nu NH_2$ : 3350 cm$^{-1}$, $\nu C = O$ : 1800–1760 cm$^{-1}$ broad (β-lactam)

b. After dissolving the 6-aminopenicillanic acid 1-oxo-1,3-dihydro-isobenzofuran-3yl ester prepared above in 35 ml of dichloromethane, 2.5g of D(−)-α-phenylglycylchloride hydrochloride and 20 ml of a dichloromethane solution containing 1.4 ml of triethylamine were added alternately to the solution with stirring under cooling to temperatures between −5°C to −10°C to maintain the reaction mixture at a weak acid state (to show a pH of about 3 when the reaction mixture was tested by a pH test paper wetted with water).

Thereafter, the reaction mixture was stirred for further 2 hours at the same temperature as above, mixed with 30 ml of cold and saturated aqueous solution of sodium chloride and stirred, the mixture was allowed to stand to form an aqueous layer and dichloromethane layer. The dichloromethane layer was separated, washed with cold and saturated aqueous solution of sodium chloride, dried over anhydrous magnesium sulfate, and concentrated under reduced pressure at a low temperature to provide an oily residue. The residue was washed with about 50 ml of ether and after recovering the insoluble solid matters by filtration, the solid matters were dissolved in 50 ml of water. The solution was washed with 30 ml of ethyl acetate, saturated with sodium chloride, and then the oily product thus formed was extracted twice each with 30 ml of dichloromethane. The dichloromethane extracts were combined each other and the mixture was washed twice each with saturated aqueous solution of sodium chloride, dried over anhydrous sodium sulfate, and concentrated under reduced pressure at a low temperature. When ether was added to the residue thus obtained with stirring, crystals were precipitated. The crystals were recovered by filtration, washed with a small amount of ether, and dried to provide 3.1g of white powdery ampicillin 1-oxo-1,3-dihydro-isobenzofuran-3-yl ester hydrochloride having a melting point of 154°–157°C (decomposed) with a yield of 52%.

| Elemental analysis as $C_{24}H_{24}O_6N_3SCl$: | | | | |
|---|---|---|---|---|
| | C(%) | H(%) | N(%) | Cl(%) |
| Calculated: | 55.65 | 4.67 | 8.11 | 6.84 |
| Found: | 55.39 | 4.91 | 7.77 | 6.70 |

EXAMPLE 5 a. After suspending 37.2g of benzylpenicillin potassium and 5g of potassium bicarbonate in 200 ml of dimethyl sulfoxide, 16.3g of 2-bromo-5-oxo-2,5-dihydrofuran was added dropwise to the suspension with stirring at room temperature over a period of 30 minutes and then the mixture was stirred for 2 hours at room temperature.

After the reaction was over, the reaction mixture was dispersed in about 1 liter of ice water and the crystals thus formed were recovered by filtration and washed with water. The crystals were dissolved in 300 ml of dichloromethane and after washing the solution with 5% aqueous solution of sodium chloride, activated carbon was added to the solution and filtered.

The filtrate was dried over anhydrous magnesium sulfate and concentrated under a reduced pressure. The residual solid matters were washed with ether and then petroleum ether and dried to provide 35g of the light yellow powder of benzylpenicillin 5-oxo-2,5-dihydro-2-furyl ester with a yield of 84%.

$[\alpha]_D^{20} = + 158°$ (C = 1, CHCl$_3$)

The product was a mixture of two diasteromers and they could be separated each other by the following manner.

That is, by recrystallizing the product from ethyl acetate, 15.4g of the whtie crystals of benzylpenicillin 5-oxo-2,5-dihydro-2-furyl ester having a melting point of 166°–168°C were obtained.

$[\alpha]_D^{20} = + 118°$ (C = 1, CHCl$_3$)

Infrared absorption spectra: $\nu$NH : 3320 cm$^{-1}$, $\nu$C = O : 1800–1765 cm$^{-1}$ broad (lactone, β-lactam and ester), $\nu$C = O : 1680 cm$^{-1}$ (amide)

Nuclear magnetic resonance absorption spectra (CDCl$_3$): δ: 1.49(6H), 3.65(2H), 4.40(1H), 5.63(2H), 6.07(1H), 6.37(1H), 7.05(1H), 7.34(5H), 7.39(1H).

Then, the mother liquer in the above recrystallization was concentrated under reduced pressure and the oily residue thus obtained was purified by subjecting it to a silica gel column chromatography using a 1 : 1 mixture of ethyl acetate and benzene as the developing solution to provide 11g of the yellowish powder of benzylpenicillin 5-oxo-2,5-dihydro-2-furyl ester having a melting point of 85°–90°C.

$[\alpha]_D^{20} = + 185°$ (C = 1, CHCl$_3$)

Infrared absorption spectra: agree with whose of the above compound showing $[\alpha]_D^{20} = + 118°$ (C = 1, CHCl$_3$):

Nuclear magnetic resonance absorption spectra (CDCl$_3$): δ : 1.49(6H), 3.65(2H), 4.43(1H), 5.59(2H), 6.11(1H), 6.49(1H), 6.99(1H), 7.35(5H), 7.39(1H).

b. After dissolving in 80 ml of dichloromethane 8.32g of the benzylpenicillin 5-oxo-2,5-dihydro-2-furyl ester showing $[\alpha]_D^{20} = + 118°$, 8.25 ml of N,N-dimethylaniline was added to the solution and the mixture was cooled to −25°C. Then, 4.6g of phosphorus pentachloride was added thereto and the reaction mixture was stirred for 1.5 hours at −25°C ± 5°C. Thereafter, 50 ml of methanol was added dropwise to the mixture at the same temperature as above and the mixture was further stirred for 3 hours, whereby a solution containing the iminoether compound thus formed was obtained. To the solution was added 13.8 ml of N,N-dimethylaniline and then 5.0g of D(−)-α-phenylglycylchloride hydrochloride was added little by little to the mixture with stirring at −25°C ± 5°C over 1 hour period. Then, the mixture was stirred for 2 hours at the same temperature and allowed to stand overnight at temperature of −20°C to −25°C.

The reaction mixture thus obtained was diluted with 80 ml of dichlormethane, 50 ml of cold and saturated aqueous solution of sodium chloride was added to the solution, and after stirring the mixture sufficiently, the mixture was filtered. The filtrate was allowed to stand to form an aqueous layer and a dichloromethane layer and the dichloromethane layer was separated. The dichloromethane layer was washed twice each with 20 ml of cold and saturated aqueous solution of sodium chloride, dried over anhydrous magnesium sulfate, and concentrated under reduced pressure. The oily residue thus formed was washed with ether and the insoluble solid matters were dissolved in 100 ml of water. The aqueous solution was washed thrice each with 50 ml of ethyl acetate and saturated with sodium chloride with stirring, thereby precipitates were formed.

The precipitates were recovered by filtration, dissolved in dichloromethane containing methanol, and the solution was dried over anhydrous magnesium sulfate and concentrated under reduced pressure at a low temperature, whereby crystals were obtained. The crystals were recrystallized from a mixture of dichloromethane and isopropyl alcohol to provide 6.25g of ampicillin 5-oxo-2,5-dihydro-2-furyl ester hydrochloride having a melting point of 192°–193°C (decomposed). The crystals were like white fine prisms. The yield for the product was 67%.

$[\alpha]_D^{20} = +175° (C = 1, H_2O)$

Elemental analysis as $C_{20}H_{21}N_3O_3S·HCl$:

| | C(%) | H(%) | N(%) | S(%) | Cl(%) |
|---|---|---|---|---|---|
| Calculated: | 51.34 | 4.74 | 8.94 | 7.58 | 6.85 |
| Found: | 50.58 | 4.93 | 8.61 | 7.45 | 6.75 |

Infrared absorption spectra (KBr): $\nu NH_3^{++}$: 3200 cm$^{-1}$, $\nu NH_2^+$: 2700–2600 cm$^{-1}$, $\nu C = 0$ : 1685 cm$^{-1}$ (amide) $\nu C = 0$ : 1780–1760 cm$^{-1}$ broad ($\beta$-lactam, lactone and ester)

Nuclear magnetic resonance spectra (CDCl$_3$—CD$_3$OD): $\delta$ : 1.49(6H), 4.41(1H), 5.22(1H), 5.52(2H), 6.42(1H), 7.08(1H), 7.50(5H), 7.55(1H)

By following the same procedure as above using the benzylpenicillin 5-oxo-2,5-dihydro-2-furyl ester showing $[\alpha]_D^{20} = +185° (C = 1, CHCl_3)$, the white powdery ampicillin 5-oxo-2,5-dihydro-2-furyl ester hydrochloride showing $[\alpha]_D^{20} = 184° (C = 1, H_2O)$ was obtained with a yield of 56%. The melting point of the product was 154°–160°C (decomposed).

Infrared absorption spectra, nuclear magnetic resonance absorptions spectra, and the results of thin layer chromatographic analysis of the product agree with those of the compound showing $[\alpha]_D^{20} = +175° (C=1, H_2O)$.

EXAMPLE 6 a. A mixture of 6.6g of 2-hydroxy-3,4-dimethyl-5-oxo-2,5-dihydrofuran and 10 ml of thionyl chloride was stirred for 2 hours at room temperature. By concentrating the reaction mixture under reduced pressure, 7.5g of light-yellowish oily 2-chloro-3,4-dimethyl-5-oxo-2,5-dihydrofuran was obtained.

b. After suspending 19g of benzylpenicillin potassium and 3g of potassium bicarbonate in 100 ml of dimethyl sulfoxide, 7.5g of the 2-chloro-3,4-dimethyl-5-oxo-2,5-dihydrofuran obtained in the above step (a) was added dropwise to the suspension over a period of 30 minutes and the mixture was stirred for 2 hours at room temperature.

The reaction mixture was dispersed in about 500 ml of ice water and he crystals thus formed were recovered by filtration and washed with water. The crystals were, then, dissolved in 100 ml of dichloromethane and the solution was washed thrice each with 50 ml of water. The dichloromethane layer was dried over anhydrous magnesium sulfate and concentrated under reduced pressure. By recrystallizing the residue thus obtained from a mixture of benzene and ether, 17.7g of white crystalline benzylpenicillin 3,4-dimethyl-5-oxo-2,5-dihydro-2-furyl ester having a melting point of 115–120°C was obtained with a yield of 78%.

Infrared absorption spectra (KBr): $\nu NH_3^+$: 3350 cm$^{-1}$ broad, $\nu C = 0$ : 1790–1750 cm$^{-1}$ (lactone, $\beta$-lactam and ester), $\nu C = 0$ : 1675 cm$^{-1}$ (amide).

Nuclear magnetic resonance absorption spectra (CDCl$_3$): $\delta$ : 1.52(6H), 1.90(3H), 1.98(3H), 3.64(2H), 4.42(1H), 5.58(2H), 6.09(1H), 6.75(1H), 7.35(5H)

c. After dissolving 4.44g of the benzylpenicillin 3,4-dimethyl-5-oxo-2,5-dihydro-2-furyl ester prepared above step (b) in 50 ml of dicholoromethane, 4.12 ml of N,N-dimethyaniline was added to the solution and the mixture was cooled to −25°C.

Then, 2.3g of phosphorus pentachloride was added to the mixture and the reaction mixture was stirred for 1.5 hours at −25°C ± 5°C. Thereafter, 40 ml of methanol was added dropwise to the mixture at the same temperature as above and the mixture was stirred for further 2.5 hours, whereby a solution containing the iminoether compound thus formed was obtained.

The solution was mixed with 6.86 ml of N,N-dimethylanilino and then 2.5g of D(−)-α-phenylglycylchloride hydrochloride was added in a few steps to the mixture with stirring at −25°C ± 5°C. over one hour period. After stirring the mixture for 2 hours at the same temperature as above, the mixture was allowed to stand for 16 hours at temperatures of −20°C to −25°C. The reaction mixture was mixed with 50 ml of cold and saturated aqueous solution of sodium chloride and after stirring the mixture sufficiently at temperatures lower than 0°C, the mixture was allowed to stand to form an aqueous layer and a dichloromethane layer.

The dichloromethane layer was separated, washed with cold and saturated aqueous solution of sodium chloride, dried over anhydrous magnesium sulfate, and concentrated under reduced pressure at a low temperature to provide an oily residue. The residue thus obtained was washed with petroleum other and the insoluble glutinous material was separated by decantation, and dissolved in 50 ml of water. The aqueous solution was washed thrice each with 30 ml of ethyl acetate, saturated with sodium chloride, and the oily material thus formed was extracted twice each with 30 ml of dichloromethane. The dichloromethane extracts were combined each other. The mixture was washed with saturated aqueous solution of sodium chloride, dried over anhydrous sodium sulfate, and concentrated under reduced pressure at a low temperature until the volume became about ⅓ of the original volume. Then, isopropanol was added until the solution became turbid and the solution was concentrated further until crystals were formed. The mixture was allowed to stand overnight at about 4°C. The crystals were recovered by filtration, washed with a small amount of isopropanol and then ether, and dried to provide 4.6g of white powdery ampicillin 3,4-dimethyl-5-oxo-2,5 -dihydro-2-furyl ester hydrochloride.

By recrystallizing the product from dichloromethane and isopropanol as in the above case, 3.2g of the white powder crystals thereof were obtained. The melting point and the yield of the product were 150°–157°C (decomposed) and 70% respectively.

Infrared absorption spectra (KBr): $\nu NH_3^+$: 3180 cm$^{-1}$, $\nu NH_2^+$: 2700–2600 cm$^{-1}$, $\nu C = 0$ : 1770 cm$^{-1}$ broad ($\beta$-lactam, lactone and ester), $\nu C = 0$ : 1680 cm$^{-1}$ (amide).

Nuclear magnetic resonance absorption spectra (CDCl$_3$ + CD$_3$OD): $\delta$ : 1.48(6H), 1.92(3H), 2.05(3H), 4.47(1H), 5.18(1H), 5.53(2H), 6.80(1H), 7.55(5H)

EXAMPLE 7 a. To 12.6g of 3-ethyl-2-hydroxy-4-methyl-5-oxo-2,5-dihydrofuran was added 8.13g of phosphorus tribromide with stirring under cooling to temperatures lower than 0°C. The mixture was stirred for 1 hour at 0°C and further stirred for 30 minutes at room temperature. By distilling the reaction mixture under reduced pressure, 12.1g of colorless liquid of 2-bromo-3-ethyl-4-methyl-5-oxo-2,5-dihydrofuran having a boiling point of 105°–106°C/3mmHg was obtained with a yield of 67%.

b. After suspending 30g of benzylpenicillin potassium and 5g of potassium bicarbonate in 60 ml of dimethyl sulfoxide, the solution of 10.6g of the 2-bromo-3-ethyl-4-methyl-5-oxo-2,5-dihydrofuran prepared in the step (a) in 20 ml of dimethyl sulfoxide was added dropwise to the suspension with stirring over a period of 30 minutes. Furthermore, the mixture was stirred for 5 hours at room temperature and the reaction mixture was dispersed in 500 ml of ice water, whereby crystals were formed.

The crystals were extracted thrice each with 100 ml of ethyl acetate, the extracts were combined and washed with 5% aqueous solution of sodium chloride, and activated carbon was added to the extract and filtered. The filtrate was dried over anhydrous magnesium sulfate and concentrated under reduced pressure.

The crystalline residue was mixed with n-hexane and then after recovering the product by filtration, the product was dried to provide 34.7g of white crystalline benzylpenicillin 3-ethyl-4-methyl-5-oxo-2,5-dihydro-2-furyl ester having a melting point of 45°–50°C with a yield of 94%.

Infrared absorption spectra (KBr): $\nu$NH : 3310 cm$^{-1}$, $\nu$C = 0 : 1790–1750 cm$^{-1}$ broad (lactone, $\beta$-lactam and ester), $\nu$C = 0 : 1660 cm$^{-1}$ (amide).

Nuclear magnetic resonance absorption spectra (CDCl$_3$): $\delta$ : 1.14(3H), 1.52(6H), 1.92(3H), 2.45(2H), 3.66(2H), 4.43(1H), 5.61(2H), 6.30(1H), 6.88(1H), 7.36(5).

c. After dissolving 9.2g of benzylpenicillin 3-ethyl-4-methyl-5-oxo-2,5-dihydro-2-furyl ester in 50 ml of dichloromethane, 8.25ml of N,N-dimethylaniline was added to the solution and the mixture was cooled to −25°C. To the mixture was further added 4.6g of phosphorus pentachloride and the reaction mixture was further stirred for 2 hours at −25°C ± 5°C. Then, 40 ml of methanol was added dropwise to the solution at the same temperature as above and the mixture was further stirred for 3 hours, whereby a solution containing the iminoether compound thus formed was obtained. To the solution was added 13.8 ml of N,N-dimethylaniline and then 5.0g of D(−)-α-phenylglycylchloride hydrochloride was added little by little to the mixture with stirring at −25°C ± 5°C over 1 hour period. Thereafter, the reaction mixture was stirred for 12 hours at the same temperature as above and then allowed to stand overnight at temperatures between −20°C to −25°C.

The reaction mixture was mixed with 40 ml of cold 15% aqueous solution of sodium chloride, stirred sufficiently and the mixture was allowed to stand to form an aqueous layer and a dichloromethane layer. The dichloromethane layer was separated, washed twice each with 20 ml of cold and saturated aqueous solution of sodium chloride, dried over anhydrous magnesium sulfate, and concentrated under reduced pressure. The oily residue thus formed was washed with ether and the insoluble solid matters were recovered and dissolved in 80 ml of water.

The aqueous solution was washed thrice each with 40 ml of ethyl acetate and then saturated with sodium chloride with stirring under cooling, whereby an oily material was formed. The oily material was extracted twice each with 40 ml of dichloromethane and the dichloromethane extracts were combined with each other. After adding activated carbon to the solution followed by filtration, the filtrate was washed with saturated aqueous solution of sodium chloride and dried over anhydrous magnesium sulfate. Thereafter, the filtrate was concentrated under reduced pressure until the volume thereof became about ⅓ of the original volume and after adding thereto isopropanol until the solution became slightly turbid, the mixture was concentrated under reduced pressure at a low temperature until crystals were precipitated. The crystals-containing solution was allowed to stand overnight at about 4°C, the crystals were recovered by filtration, washed with a small amounts of isopropanol and then petroleum ether, and dried to provide 6.6g of white powdery ampicillin 3-ethyl-4-methyl-5-oxo-2,5-dihydro-2-furyl ester hydrochloride having a melting point of 150°–151°C (decomposed). The yield for the product was 64%.

Infrared absorption spectra (KBr): $\nu$NH$_3^+$ : 3180 cm$^{-1}$, $\nu$NH$_2^+$ : 2700–2600 cm$^{+1}$, $\nu$C = 0 : 1790–1750 cm$^{-1}$ broad ($\beta$-lactam, lactone and ester), $\nu$C = 0 : 1680 cm$^{-1}$ (amide).

Nuclear magnetic resonance absorption spectra (CDCl$_3$ + CD$_3$OD) $\delta$ : 1.16(3H), 1.47(6H), 1.91(3H), 2.46(2H), 4.42(1H), 5.27(1H), 5.49(2H), 6.87(1H), 7.49(5H).

EXAMPLE 8 a. After dissolving 9.3g of benzylpenicillin 1-oxo-1,3-dihydro-isobenzofuran-3-yl ester in 30 ml of chloroform, 35 ml of a chloroform solution containing 2.82g of perbenzoic acid was added dropwise to the solution at temperatures lower than 10°C, and thereafter, the mixture was stirred for 15 minutes at room temperature. The reaction mixture was washed with 3% aqueous solution of sodium bicarbonate and then water, dried over anhydrous magnesium sulfate and then chloroform was distilled away from the solution under reduced pressure.

When ether was added to the residue, crystals were precipitated. By recovering the crystals by filtration, 9.2g of the white powdery crystals of benzylpenicillin sulfoxide 1-oxo-1,3-dihydro-isobenzofuran-3-yl ester having a melting point of 103°–108°C (decomposed) was obtained with a yield of 97%.

b. To 50 ml of dioxane were added 9.6g of the benzylpenicillin sulfoxide 1-oxo-1,3-dihydro-isobenzofuran-3-yl ester obtained above step a), 0.114 ml of pyridine and 244 mg of phenyldihydrogen phosphate, and the mixture was heated for 4 hours in an oil bath of 105°C. After cooling, the reaction mixture was distilled under a reduced pressure to remove chloroform. The residue thus obtained was dissolved in chloroform and the solution was washed with water, dried over anhydrous magnesium sulfate, and then the chloroform was distilled off under reduced pressure. The residue was subjected to a silica gel column chromatography and the product was isolated by using a mixture of chloroform and ethyl acetate (3 : 1 by volume ratio) as an elute. The solvent was distilled off from the effluent under reduced pressure, ether was added to the residue, and the powder thus formed was recovered by filtration to provide 5.6g of the white powdery crystals of 7-phenylacetamidodesacetoxycephalosporanic acid 1-oxo-1,3-dihydro-isobenzofuran-3-yl ester with a yield of 61%.

$[\alpha]_D^{18} = 35.8°$ (C = 1, chloroform)

Elemental analysis as C$_{24}$H$_{20}$N$_2$O$_6$S:

|  | N (%) |
|---|---|
| Calculated: | 6.03 |
| Found: | 5.92 | c. After suspending 4.6g of the 7-phenylacetamidosacetoxycephalosporanic acid 1-oxo- 1,3-dihydro-isobenzofuran-3-yl ester prepared above step (b) in 50 ml of dichloromethane, 4.12 ml of dimethyl aniline was added to the suspension. Then, 2.3g of phosphorus pentachloride was added thereto at −20°C and the reaction mixture was stirred for 2 hours at temperatures between −5°C to −10°C. To the brown transparent reaction mixtures was added dropwise 40 ml of anhydrous methanol at −20°C and thereafter, the mixture was stirred for one hour at −10°C. To the reaction mixture were further added 6.86 ml of dimethylaniline and 2.5g of D(−)-α-phenylglycylchloride hydrochloride, and then the mixture was stirred for 30 minutes at −10°C. The reaction mixture was mixed with 50 ml of saturated aqueous solution of sodium chloride and stirred for 10 minutes at 0°C, the mixture was allowed to stand to form an aqueous layer and an organic solvent layer. The organic solvent layer was separated, washed twice each with saturated aqueous solution of sodium chloride, and then the solvent was distilled off under reduced pressure. The residue was dissolved in water and the aqueous solution was washed twice each with ethyl acetate. Sodium chloride was added to the solution and the oily material thus formed was extracted with dichloromethane. After drying the extract over anhydrous magnesium sulfate, the solvent was distilled off under reduced pressure, and then ether was added to the residue thus obtained. BY recovering the powder thus formed by filtration, 2.9g of the white powder of 7-(α-aminophenylacetamido)desacetoxycephalosporanic acid 1-oxo-1,3-dihydro-isobenzofuran-3-yl ester hydrochloride was obtained with a yield of 57%.

$[\alpha]_D^{18} = +21.8$ (C = 1, methanol)

Elemental analysis as $C_{24}H_{22}N_3O_6SCl$:

|  | N (%) |
|---|---|
| Calculated: | 8.14 |
| Found: | 7.95 | d. After suspending 3g of the 7-phenylacetamidodesacetoxycephalosporanic acid 1-oxo-1,3dihydro-isobenzofuran-3-yl ester in 45 ml of dichloromethane, 2.58g of dimethyl aniline was added to the suspension. Then, 1.49g of phosphorus pentachloride was added thereto at −20°C and the reaction mixture was stirred for 2 hours at temperatures of −10°C to −20°C. To the reaction mixture was added 20 ml of methanol at above temperature, and then the mixture was stirred for one hour and thirty minutes.

To the reaction mixture were added 4.3g of dimethylaniline and 1.6g of D(−)-α-phenylglycylchloride hydrochloride, and then the mixture was stirred for 2 hours at −15°C. The reaction mixture was mixed with a saturated aqueous solution of sodium chloride and the organic layer was washed sufficiently. The organic layer was concentrated under reduced pressure, and ether was added to the residue, whereby white precipitate was formed. The precipitate thus obtained was dissolved in water and the solution was washed with ethyl acetate sufficiently, and when sodium chloride was added to the solution to form a white precipitate.

The precipitate was recovered by the filtration and recrystallized from a mixture of methanol and water (1 : 3 in volume ratio) to provide 2g of white crystals of 7(α-aminophenylacetamido)desacetoxycephalosporanic acid 1-oxo-1,3-dihydro-isobenzofuran-3-yl ester hydrochloride having a melting point of 200°–201°C (decomposed) with a yield of 60%.

$[\alpha]_D^{18} = +25.8°$ (C = 1, methanol)

Elemental analysis as $C_{24}H_{22}N_3O_6Cl.H_2O$

|  | N (%) | Cl (%) |
|---|---|---|
| Calculated: | 7.87 | 6.64 |
| Found: | 7.98 | 7.06 |

What is claimed is:

1. The oxofuryl ester derivatives of 6-α-aminophenylacetamido)penicillanic acid represented by the formula

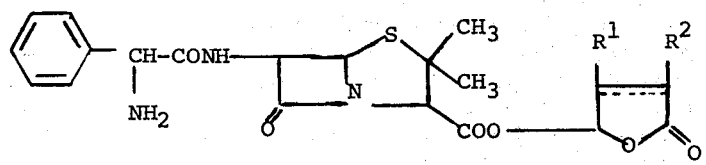

wherein $R^1$ and $R^2$, which may be the same or different, each represents hydrogen or lower alkyl, and wherein ═══ represents a single bond or a double bond, and the acid addition salts thereof.

2. 6-(α-Aminophenylacetamido)penicillanic acid 5-oxo-tetrahydro-2-furyl ester and the hydrochloride salt thereof.

3. 6-(αAminophenylacetamido)penicillanic acid 5-oxo-2,3-dihydrofuran-2-yl ester and the hydrochloride salt thereof.

4. 6-(α-Aminophenylacetamido)penicillanic acid 3,4-dimethyl-5-oxo-2,5-dihydrofuran-2-yl ester and the hydrochloride salt thereof.

5. 6-(α-Aminophenylacetamido)penicillanic acid 3-ethyl-4-methyl-5-oxo-2,5-dihydrofuran-2-yl ester and the hydrochloride salt thereof.

* * * * *

UNITED STATES PATENT OFFICE
CERTIFICATE OF CORRECTION

Patent No. 3,951,954          Dated April 20, 1976

Inventor(s)    Masuo Murakami, et al

It is certified that error appears in the above-identified patent and that said Letters Patent are hereby corrected as shown below:

Column 9, line 31:  "(-HN-)" should read --(-NH-)--.

Column 14, line 2:  "whtie" should read --white--.
          line 22: "whose" should read --those--.
          line 47: "dichlormethane" should read --dichloromethane--.

Column 15, line 5:  "$O_3$" should read --$O_6$-- (Elemental Analysis).
          line 11: "$NH_3^{++}$" should read --$NH_3^+$--.
          line 46: "he" should read --the--.
          line 65: "dicholoromethane" should read --dichloromethane--.
          line 66: "dimethyaniline" should read --dimethylaniline--.

Column 16, line 6:  "thylanilino" should read --thylaniline--.
          line 22: "other" should read --ether--.

Column 19, line 7:  "mixtures" should read --mixture--.
          line 27: "BY" should read --By--.

Column 18, last line:  "phenylacetamidosacetoxycephalosporanic" should read: --phenylacetamidodesacetoxycephalosporanic--.

UNITED STATES PATENT OFFICE
CERTIFICATE OF CORRECTION

Patent No. 3,951,954   Dated April 20, 1976

Inventor(s) Masuo Murakami, et al

It is certified that error appears in the above-identified patent and that said Letters Patent are hereby corrected as shown below:

Column 20, line 13: "when" should read --then--.

line 30 (Claim 1, line 1): "6-$\alpha$-amino" should read --6-($\alpha$-amino--.

line 47 (Claim 3, line 1): "6-($\alpha$ Amino" should read --6-($\alpha$-Amino--.

line 48 (Claim 3, line 2): "2,3-dihydrofuran" should read --2,5-dihydrofuran--.

Signed and Sealed this

Twelfth Day of October 1976

[SEAL]

Attest:

RUTH C. MASON
Attesting Officer

C. MARSHALL DANN
Commissioner of Patents and Trademarks